United States Patent [19]

Hamberger et al.

[11] Patent Number: 4,477,448
[45] Date of Patent: Oct. 16, 1984

[54] CEPHALOSPORIN DERIVATIVES AND USE AS ANTIMICROBIAL AGENTS

[75] Inventors: Helmut Hamberger; Hans Fliri, both of Wien, Austria

[73] Assignee: Sandoz Ltd., Basel, Switzerland

[21] Appl. No.: 390,323

[22] Filed: Jun. 21, 1982

Related U.S. Application Data

[63] Continuation of Ser. No. 205,198, Nov. 10, 1980, abandoned, which is a continuation-in-part of Ser. No. 121,953, Feb. 15, 1980, abandoned.

[30] Foreign Application Priority Data

Feb. 16, 1979 [CH] Switzerland ............ 1545/79
Jan. 10, 1980 [CH] Switzerland ............ 174/80

[51] Int. Cl.³ ............ A61K 31/545; C07D 501/56
[52] U.S. Cl. ............ 424/246; 544/22; 544/27; 544/28; 548/377; 548/378
[58] Field of Search ............ 544/27, 22, 28; 424/246

[56] References Cited

U.S. PATENT DOCUMENTS 4,024,137 5/1977 Cook et al. ............ 544/27

Primary Examiner—Paul M. Coughlin, Jr.
Attorney, Agent, or Firm—Gerald D. Sharkin; Richard E. Vila

[57] ABSTRACT

Novel compounds of formula I,

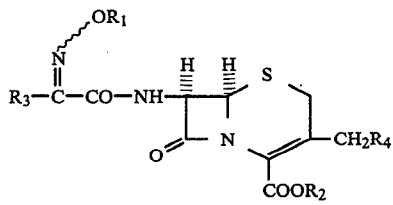

in which $R_1$ is hydrogen, alkyl, phenylalkyl, carbalkoxyalkyl, acyl, carboxyalkyl, alkoxyalkyl, hydroxyalkyl, cyanoalkyl, or carbamoylalkyl, $R_2$ is hydrogen, pivaloyloxymethyl or the residue of an easily splittable ester grouping, $R_3$ is a pyrazolyl radical, unsubstituted or mono- or di-substituted by alkyl, phenyl, alkoxy, alkylthio, carboxy, carboxyalkyl, carbamoyl, carbamoylalkyl, alkylsulphonyl, azido, acylamino, hydrazino, acylhydrazino alkylidenehydrazino, phenylidenehydrazino, in which the phenyl nucleus is unsubstituted or substituted by $NH_2$, lower alkoxy or lower alkyl, furylidenehydrazino, carbalkoxy or a group $R_5R_6N$—, in which $R_5$ and $R_6$ are the same or different and are hydrogen or alkyl, provided that the nitrogen atoms and the 4-position of the pyrazole nucleus are either unsubstituted or substituted by alkyl, phenyl, or carbalkoxy, and $R_4$ is hydrogen, acetoxy, carbamoyloxy or —S—Rh, in which Rh is a heterocyclic radical.

15 Claims, No Drawings

CEPHALOSPORIN DERIVATIVES AND USE AS ANTIMICROBIAL AGENTS

This is a continuation of application Ser. No. 205,198 filed Nov. 10, 1980, which in turn is a continuation-in-part of Ser. No. 121,953, filed Feb. 15, 1980, now both abandoned.

This invention provides compounds of formula I,

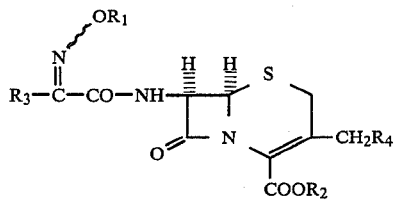

in which
- $R_1$ is hydrogen, alkyl, phenylalkyl, carbalkoxyalkyl, acyl, carboxyalkyl, alkoxyalkyl, hydroxyalkyl, cyanoalkyl, or carbamoylalkyl,
- $R_2$ is hydrogen, pivaloyloxymethyl or the residue of an easily splittable ester grouping,
- $R_3$ is a pyrazolyl radical, unsubstituted or mono- or di-substituted by alkyl, phenyl, alkoxy, alkylthio, carboxy, carboxyalkyl, carbamoyl, carbamoylalkyl, alkylsulphonyl, azido, acylamino, hydrazino, acylhydrazino, alkylidenehydrazino, phenylidenehydrazino, in which the phenyl nucleus is unsubstituted or substituted by $NH_2$, lower alkoxy or lower alkyl, furylidenehydrazino, carbalkoxy or a group $R_5R_6N—$, in which $R_5$ and $R_6$ are the same or different and are hydrogen or alkyl, provided that the nitrogen atoms and the 4-position of the pyrazole nucleus are either unsubstituted or substituted by alkyl, phenyl, or carbalkoxy, and
- $R_4$ is hydrogen, acetoxy, carbamoyloxy or $—S—Rh$, in which $Rh$ is a heterocyclic radical.

The group $—OR_1$ in the compounds of the invention may be in the syn or anti-configuration. It is to be understood that the invention includes both isomeric forms as well as mixtures thereof. The syn isomers or isomeric mixtures in which the syn isomer predominates, e.g. to the extent of at least 75%, more particularly at least 90%, are however preferred.

In the radical $R_3$, the pyrazole nucleus may, when the nitrogen atoms thereof are unsubstituted, exist in tautomeric forms:

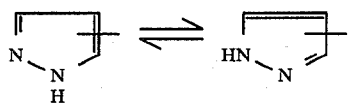

The position of the tautomeric equilibrium will of course depend on known factors such as temperature, aggregation condition, solvent, pH and substituents on the nucleus. Naturally, the invention is not limited to any particular tautomeric form.

The invention also provides processes for the production of compounds of formula I, comprising
(a) Producing a compound of formula Ia,

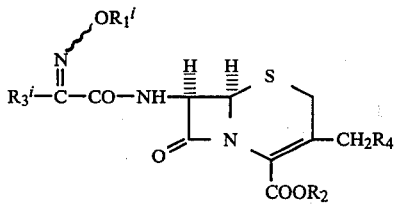

in which
- $R_2$ and $R_4$ are as defined above,
- $R_1{}^I$ has the same significance as $R_1$, defined above, except that it may not be carboxyalkyl, and
- $R_3{}^I$ has the same significance as $R_3$, defined above, except that it may not be carboxy-, carboxyalkyl-, amino-, monoalkylamino-, hydrazino- or aminophenylidenehydrazino-substituted pyrazolyl, by reacting a compound of formula II,

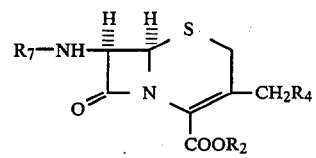

in which
- $R_2$ and $R_4$ are as defined above, and
- $R_7$ is hydrogen or an amino protecting group, with a compound of formula III,

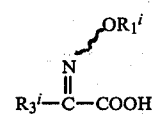

in which $R_1{}^I$ and $R_3{}^I$ are as defined above, or a reactive derivative thereof, (b) producing a compound of formula Ib,

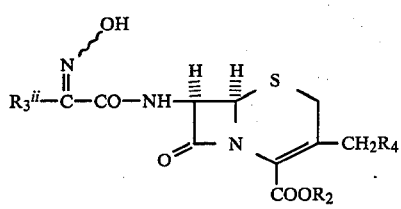

in which
- $R_2$ and $R_4$ are as defined above, and
- $R_3{}^{II}$ has the same significance as $R_3$, defined above, except that it may not be azido or acylamino-substituted pyrazolyl, by hydrogenating a compound of formula Ic,

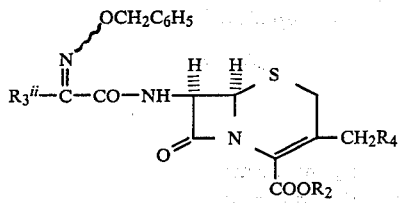

in which $R_2$, $R_3{}^{II}$ and $R_4$ are as defined above, (c) producing a compound of formula Id,

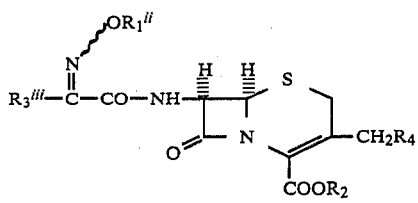

in which $R_2$ and $R_4$ are as defined above, and either
$R_1^{II}$ is carboxyalkyl, and
$R_3^{III}$ is the same as $R_3$, defined above, except that it may not be $R_5R_6N-$, carbamoyl- or carbamoylalkyl-substituted pyrazolyl,
or $R_1^{II}$ is the same as $R_1$, defined above, except that it may not be carbamoylalkyl, and
$R_3^{III}$ is carboxy- or carboxyalkyl-substituted pyrazolyl,
by hydrolysing a compound of formula Ie,

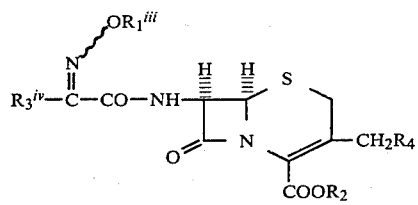

in which $R_2$ and $R_4$ are as defined above, and either
$R_1^{III}$ is carbamoylalkyl, and
$R_3^{IV}$ is the same as $R_3$, defined above, except that it may not be $R_5R_6N$-substituted pyrazolyl,
or $R_1^{III}$ is the same as $R_1$, defined above, and
$R_3^{IV}$ is carbamoyl- or carbamoylalkyl-substituted pyrazolyl, or
(d) producing a compound of formula If,

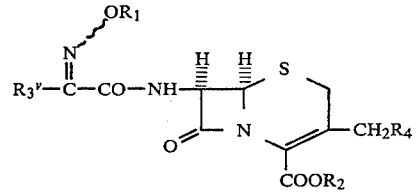

in which $R_1$, $R_2$ and $R_4$ are as defined above, and $R_3^V$ is the same as $R_3$, defined above, except that the pyrazolyl radical contains at least one $-NH_2$ substituent, by hydrogenating a compound of formula Ig,

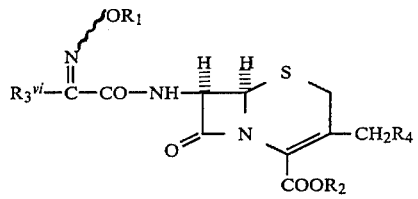

in which $R_1$, $R_2$ and $R_4$ are as defined above, and $R_3^{VI}$ is the same as $R_3$, defined above, except that the pyrazolyl radical contains at least one azido or benzyloxycarbonylamino substituent.

Suitable reactive derivatives of the acid of formula III for use in process (a) include acid halides or acid anhydrides, for example with oxalic or pivalic acid or carbonic acid half-esters, activated complexes with dimethyl formamide/phosphorous oxychloride, acid azides or activated esters, for example derived from phenols, cyclic N-hydroxyimides or heterocyclic thiols, e.g. 2-pyridenethiol or 2,2'-dithiopyridine. The process is suitably effected by dissolving or suspending the compound III or derivative thereof in an inert solvent, such as chlorinated hydrocarbon, e.g. dichloromethane, or an acid ester, e.g. ethyl acetate. This solution or suspension is then suitably added to a solution or suspension of the compound II in an inert solvent, e.g. an acid ester, such as ethyl acetate, or an aromatic hydrocarbon, e.g. toluene. The process is conveniently effected at a temperature of, e.g. $-20°$ C. to room temperature. When the compound of formula III is used in free acid form, a condensation agent, such as dicyclohexyl carbodiimide or carboxy/diimidazole is suitably added.

Where a compound of formula Ia, in which $R_2$ is hydrogen is desired, it is convenient to protect the carboxylic acid function in the starting material of formula II prior to reaction with the compound of formula III or derivative thereof. Conventional methods of protection may be employed. Preferred protecting groups include trialkylsilyl groups, in particular trimethylsilyl, which may be introduced by reaction, e.g. with N,O-bis-trimethylsilylacetamide.

The hydrogenation in processes (b) and (d) may be carried out in conventional manner, for example in an inert solvent, e.g. water, and in the presence of a catalyst such as Pd/activated carbon.

Process (c) is suitably effected with an acid, preferably nitrous acid. Conveniently the compound Ie may be dissolved in a mixture of acetic acid and dilute sulphuric acid and a solution of an alkyl nitrite, e.g. in water, may then be added at a low temperature, e.g. at about 0° C.

The resulting compounds of formula I may be isolated and purified using conventional techniques. Where required, free acids ($R_2=H$) may be converted into salt forms, e.g. alkali metal, alkaline earth metal and ammonium salt forms in conventional manner, and vice versa.

It will also be appreciated that various compounds of formula I may be inter-converted. For example, free acids ($R_1=H$) may be esterified in conventional manner to obtain compounds in which $R_2$ is the residue of an easily splittable ester grouping. The latter may themselves be split in conventional manner to obtain free acids.

The compounds of formula I are preferably in the form of syn isomers. If starting materials are employed in the form of syn isomers, then the product may be a syn isomer or a mixture of the syn and an anti-isomer, depending on the type of substituents and reaction conditions. Individual isomers may be isolated from mixtures by chromatographic or enzymatic methods.

Chromatographic separation may be effected in conventional manner, for exampe by column chromatography with a suitable eluant, e.g. acetonitrile/water or chloroform/methanol. The uniform fractions may be pooled and purified.

The syn isomers may be obtained by enzymatic separation, which depends on the hitherto unknown property that syn isomers are stable against β-lactamases, while the anti-isiomers are, to a large extent, decomposed. By treatment of the isomeric mixture with a β-lactamase, e.g. with an enzyme of the Type III, 1320 or of the O-Type, against which the anti-isomer is not stable, the latter can be removed. For example, the mixture may be incubated with a β-lactamase, e.g. at about 30° C. and for about 5 hours. The syn isomer may then be isolated and purified in conventional manner.

The starting materials of formula III are new and may for example be produced in accordance with the following reaction schemes:

Scheme I:

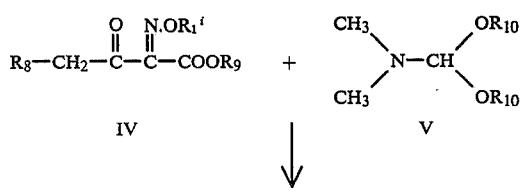

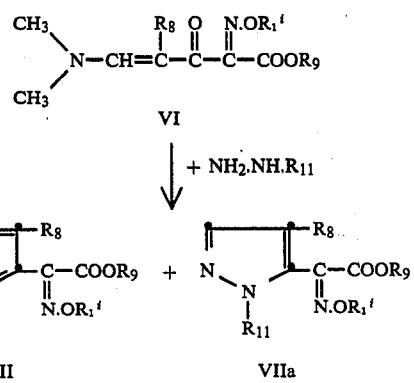

Scheme II:

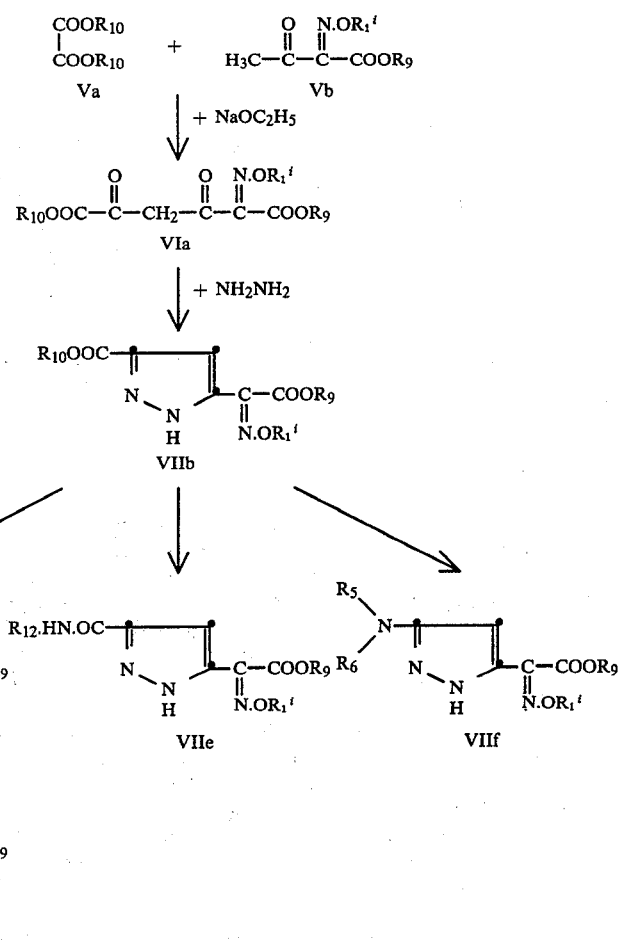

Scheme III:

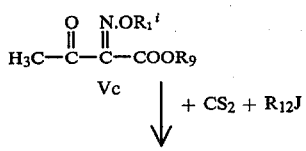

Scheme III:

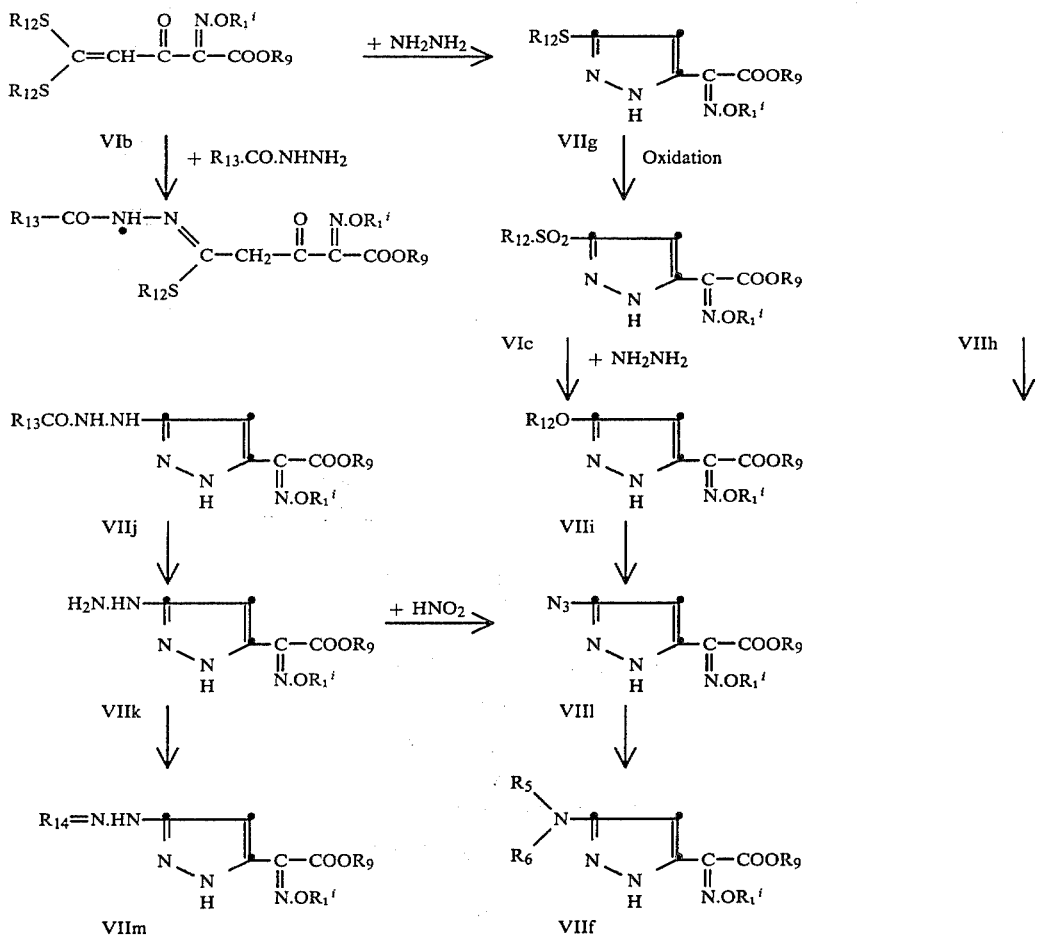

In these formulae, $R_8$ is hydrogen, alkyl or phenyl, $R_9$ is alkyl, benzyl, 4-nitrophenyl, 2,2,2-trichloroethyl, phenyl or substituted phenyl, $R_{10}$ is alkyl, $R_{11}$ is hydrogen, alkyl or phenyl, $R_{12}$ is lower alkyl, $R_{13}$ is alkyl, alkoxy, phenyl, phenylalkyl, or phenylalkoxy, and $R_{14}$ alkylidene, furylidene or phenylidene, optionally substituted by —$NH_2$ or lower alkyl or alkoxy.

The resulting compounds of formulae VII to VIIg may be converted into the corresponding compounds of formula III in conventional manner, by hydrolysis. Compounds unsubstituted on the nitrogen atoms or at the 4-position of the pyrazole ring may be alkylated or phenylated in conventional manner at any appropriate stage in the syntheses described, particularly at a point where there are no other sensitive groups in the molecule.

The compounds of formula I are useful as chemotherapeutic agents, in particular anti-microbial agents, as indicated by their inhibiting effect against various bacteria, e.g. *Staphylococcus aureus, Streptococcus pyogenes, Streptococcus faecalis, Escheria coli, Proteus vulgaris, Proteus mirabilis, Proteus morganii, Shigella dysenteria, Shigella sonnei, Shigella flexneri, Alcaligenes faecalis, Klebsiella aerogenes, Klebsiella pneumoniae, Serrata marcescen, Salmonella Heidelberg, Salmonella typhimurium, Salmonella enteritidis,* and *Neisseria gonorrhoae,* in vitro in the series dilution test at concentrations of, for example 0.01 to 50 μg/ml, and in vivo in the mouse at dosages of for example about 0.1 to 100 mg/kg of animal body weight. The compounds are therefore useful as antibacterially active antibiotics.

For this use, the effective dosage will of course vary depending on the particular compound employed, mode of administration and the treatment desired. However, in general, satisfactory results can be obtained when the compounds are administered at a daily dosage of from about 10 to 100 mg/kg of animal body weight, suitably given in divided doses two to four times daily. For most larger mammals, the total daily dose is from about 1 to 6 g and dosage forms suitable for internal administration suitably contan 250 to 3000 mg of the compound in admixture with a solid or liquid pharmaceutical carrier or diluent.

The compounds in which $R_2$ is H may be employed in free acid form or in the form of pharmaceutically acceptable salts, which salt forms have the same order of activity as the free acids. Suitable salt forms include alkali and alkaline earth metal and ammonium salt forms.

The compounds may be admixed with conventional pharmaceutically acceptable diluents and carriers, and administered in such forms as tablets or capsules.

Compounds of formula I, whose production is not described above, i.e. compounds in which $R_1$ is carboxyalkyl and $R_3$ is carbamoyl-, carbamoylalkyl-, monoalkylamino- or dialkylamino-substituted pyrazolyl, and in which $R_1$ is carbamoylalkyl and $R_3$ is carboxy- or carboxyalkyl-substituted pyrazolyl, may be prepared by analogous or known methods. However, these compounds are not of especial interest and the preferred compounds of formula I excludes these compounds.

In the compounds of formula I, "alkyl" radicals or radicals containing alkyl radicals, preferably contain 1 to 4 carbon atoms in the alkyl parties thereof, more preferably 1 to 2 carbon atoms.

$R_1$ can be hydrogen. Alternatively, it may be alkyl, such as methyl or phenylalkyl such as benzyl. Suitable carbalkoxyalkyl radicals include carbalkoxymethyl radicals, e.g. carbethoxymethyl. Suitable acyl radicals include $C_{2-5}$alkanoyl or alkoxycarbonyl. Carboxyalkyl may for example be carboxymethyl. Carbamoylalkyl may for example be carbamoylmethyl. Cyanoalkyl may be cyanomethyl; hydroxyalkyl is suitably hydroxymethyl and alkoxyalkyl is is suitably alkoxymethyl, e.g. methoxymethyl. In preferred compounds $R_1$ is alkyl, carbalkoxyalkyl and carbamoylalkyl.

$R_2$ may be hydrogen. Alternatively, it may be pivaloyloxymethyl. Suitable easily splittable ester groups are well-known in the cephalosporin field and include acetoxymethyl, 1-acetoxyethyl, 1-ethoxycarbonyloxyethyl, 5-indanoyl or, preferably hexanoyloxymethyl, phthalidyl, carbethoxymethoxymethyl or 3-carbethoxy-1-acetonyl.

The preferred pyrazolyl groups for $R_3$ are linked to the

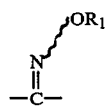

radical at the 3- or 5-position of the nucleus. Preferably, the nucleus is unsubstituted in the 4-position.

The nitrogen atom available for substitution may be unsubstituted. Alternatively, it may be substituted by alkyl, e.g. methyl; by phenyl; or by carbalkoxy, e.g. isobutyloxycarbonyl.

The remaining position of the pyrazole nucleus may be unsubstituted. Alternatively, it may be substituted by alkyl; by phenyl; by alkoxy, e.g. ethoxy; by alkylthio, e.g. methylthio; by carboxy; by carboxyalkyl; by carbamoyl; by carbamoylalkyl; by alkylsulphonyl, e.g. methylsulphonyl; by azido; by acylamino, in particular $C_{2-5}$alkanoylamino or $C_{1-4}$alkoxy- or benzyloxy-carbonylamino; by hydrazino; by acylhydrazino, e.g. $C_{2-5}$alkanoylhydrazino; by alkylidenehydrazino; by phenylidenehydrazino, in which the phenyl is unsubstituted or substituted by $NH_2$ or lower alkyl or alkoxy; by furylideneaminohydrazino; by carbalkoxy, e.g. carbethoxy; or by a radical $R_5R_6N$—. The groups $R_5$ and $R_6$ are preferably hydrogen. One or both may however be alkyl.

The preferred radical $R_3$ is unsubstituted pyrazolyl-3 (or -5).

$R_4$ may be hydrogen. In another group of compounds, it is acetoxy. In a third group it is carbamoyloxy. Preferably, however, it is —S—Rh. The preferred heterocyclic radical Rh is 1-methyltetrazolyl.

Particularly preferred compounds include the following compounds: 7-{[(pyrazolyl-3)-syn-methoxyimino]acetylamino}-3-desacetoxy-3-[1-methyl-tetrazolyl-5-thio]cephalosporanic acid sodium salt, 7-{[(pyrazolyl-3)-syn-methoximino]acetylamino}-3-desacetoxy-3-(1-methyltetrazolyl-5-thio)cephalosporanic acid pivaloyloxymethyl ester, 7-{[(pyrazolyl-3)-syn-carbethoxymethoximino]acetylamino}-3-desacetoxy-3-(1-methyl-tetrazolyl-5-thio)cephalosporanic acid, 7-{[(pyrazolyl-3)-syn-carbethoxymethoximino]acetylamino}-3-desacetoxy-3-[1-methyltetrazolyl-5-thio]cephalosporanic acid pivaloyloxymethyl ester and 7-{[(pyrazolyl-3)-syn-carbamoylmethoximino]acetylamino}-3-desacetoxy-3-(1-methyltetrazolyl-5-thio)cephalosporanic acid.

Insofar as the production of starting materials is not described, these may be produced by conventional methods.

The following Examples in which all temperatures are indicated in °C. illustrate the invention. Unless otherwise indicated, the compounds of formula I are obtained in the form of syn/anti isomeric mixtures.

EXAMPLE 1

7-[[(1-Methylpyrazolyl-5)methoxyimino]acetylamino]-cephalosporanic acid (Process a)

1.5 ml of dry dimethylformamide and 1.7 ml of phosphorous oxychloride are warmed at 40° for 1 hour. After addition of 50 ml of dry methylene dichloride, the solution is evaporated to dryness and the residue is taken up in 50 ml of ethyl acetate. 3.6 g of (1-methylpyrazolyl-5)methoxyimino-acetic acid are added at 0° and the mixture is stirred at 0° for 1 hour. This solution is added at −20° to a solution of 5.4 g of 7-aminocephalosporanic acid in 100 ml of ethyl acetate and 15 ml of N,O-bistrimethylsilylacetamide are added dropwise. After a reaction time of 3 hours at −20° C., 70 ml of saturated sodium chloride solution are added, the organic phase is separated and the aqueous phase is extracted twice with each time 100 ml of ethyl acetate. The combined ethyl acetate phases are extracted twice with each of 1N hydrochloric acid, saturated sodium chloride solution and saturated sodium bicarbonate solution. The combined bicarbonate phases are freed from solvent residues is vacuo and brought to pH 2 with 2N hydrochloric acid. The precipitated crystals are filtered, washed with water and dried, to obtain the heading compound, m.p. 110°–112°. The sodium salt thereof may be prepared by dissolving 5 g of the acid in 980 mg of sodium bicarbonate/100 ml of water, extracting twice with ethyl acetate and lyophilising the aqueous phase. M.P. of sodium salt: 157° (decomp.).

EXAMPLE 2

7-[[(Pyrazolyl-3)methoxyimino]acetylamino]cephalosporanic acid (Process a)

To a suspension of 1.69 g of (pyrazolyl-3)methoxyimino-acetic acid and 2.3 g of 2,2'-dithiodipyridine in 50 ml of dry methylene dichloride are added, at room temperature, 2.7 g of triphenylphosphine and the mixture is stirred for 30 minutes at room temperature. The resulting suspension is mixed at room temperature with a solution of 2.72 g of 7-aminocephalosporanic acid in 100 ml of dry toluol and 7 ml of N,O-bis-trimethylsilylacetamide and the mixture is stirred at room temperature for 50 hours. After evaporation to dryness, the residue is taken up in 200 ml of ethyl acetate and extracted successively 5 times with 50 ml of 1N hydrochloric acid, 5 times with 50 ml of saturated sodium chloride solution and twice with 50 ml of saturated sodium bicarbonate solution. The purified bicarbonate phases are further extracted three times with ethyl acetate, freed from solvent residue on a rotary evaporator and finally brought to pH 2 with concentrated hydrochloric acid. The heading compound, m.p. 112° (decomp.) is obtained by extraction with ethyl acetate and may be converted to the sodium salt by dissolving 424 mg of the acid in 84 mg of sodium bicarbonate/10 ml of water, and lyophilising. M.P. of the sodium salt: 250° (decomp.).

In manner analogous to that described in Examples 1 and 2, employing appropriate starting materials, in approximately equivalent amounts, the compounds set out in the following table may be obtained (Examples 3 to 27):

| EX. | $R_1$ | $R_2$ | $R_3$ | $R_4$ | M.P. |
|-----|-------|-------|-------|-------|------|
| 3 | —$CH_2COOC_2H_5$ | H | [pyrazole] | $-S-$[methyl-thiadiazole] | 122–125° (decomp.) |
| 4 | —$CH_2CONH_2$ | H | " | —O.CO.$CH_3$ | 135° (decomp.) |
| 5 | —$CH_2CN$ | H | " | —O.COCH$_3$ | |
| 6 | —$CH_2.C_6H_5$ | H | " | —O.COCH$_3$ | 190° (decomp.) |
| 7 | —$CH_2OCH_3$ | H | " | —O.COCH$_3$ | |
| 8 | —$CH_3$ | H | " | H | >125° (decomp.) |
| 9 | —$CH_3$ | H | " | —O.CO.$NH_2$ | |
| 10 | —$CH_3$ | H | $H_2N.CO$-[pyrazole] | —O.CO.$CH_3$ | |
| 11 | —$CH_3$ | H | [pyrazole-$C_6H_5$] | —O.CO.$CH_3$ | 185–190° (decomp) |
| 12 | —$CH_3$ | H | $C_6H_5CH_2O.CO.NH$-[pyrazole] | $-S-$[methyl-thiadiazole] | |
| 13 | —$CH_3$ | H | $CH_3S$-[pyrazole] | —O.CO.$CH_3$ | 147–151° (decomp) |
| 14 | —$CH_3$ | H | [pyrazole] | $-S-$[methyl-thiadiazole] | 146–148° (decomp) |
| 15 | —$CH_3$ | H | [N-methyl pyrazole] | " | |
| 16 | —$CH_3$ | H | [N-methyl pyrazole] | " | 150–155° (decomp) |
| 17 | —$CH_3$ | H | [furyl]—CH=N.NH-[pyrazole] | " | |

-continued

| EX. | $R_1$ | $R_2$ | $R_3$ | $R_4$ | M.P. |
|---|---|---|---|---|---|
| 18 | —CH$_3$ | H | (CH$_3$)$_2$CH.CH$_2$.O.C(O)—NH— attached to pyrazolyl (N—N ring) | " | |
| 19 | —CH$_3$ | H | 3-N$_3$, 1-CH$_3$-pyrazolyl | " | |
| 20 | —CH$_3$ | H | 3-CH$_3$SO$_2$-pyrazolyl (NH) | " | |
| 21 | —CH$_3$ | H | 3-H$_2$N.NH-pyrazolyl (NH) | " | |
| 22 | —CH$_3$ | H | 3-(H$_5$C$_2$.O.CO)-pyrazolyl (NH) | —O.CO.CH$_3$ | 175–185° (decomp) |
| 23 | —CH$_2$CONH$_2$ | H | pyrazolyl (NH) | —S-(1-methyltetrazol-5-yl) | >142° |
| 24 | H | H | " | " | >80° (decomp.) |
| 25 | CH$_3$ | H | 3-N$_3$, 1-CH$_3$-pyrazolyl | —O.CO.CH$_3$ | |
| 26 | CH$_3$ | H | 3-H$_2$N, 1-CH$_3$-pyrazolyl | " | |
| 27 | CH$_3$ | H | 3-H$_2$N, 2-CH$_3$-pyrazolyl | " | |

EXAMPLE 28

7-[[(3-Azidopyrazolyl-5)-methoxyimino]acetylamino]-3-desacetoxy-3-(1-methyltetrazolyl-5-thio)cephalosporanic acid (Process a)

A mixture of 0.154 ml of dry dimethylformamide and 0.175 ml of oxalylchloride in 50 ml of dry dichloromethane is stirred at 0° for 30 minutes. The mixture is evaporated to dryness in the absence of moisture and the residue is taken up in 50 ml of dry dichloromethane. The solution is mixed with a solution of 420 mg of (3-azidopyrazolyl-5)methoxyimino-acetic acid and 0.298 ml of 1,5-diazobicyclo[5,4,0]undec-5-en in 50 ml of dry methylene dichloride and the mixture is stirred for 30 minutes at 0°. The solution is added to a solution of 544 mg of 7-amino-3-desacetoxy-3-(1-methyltetrazolyl-5-thio)cephalosporanic acid in 50 ml of dry methylene dichloride and 0.5 ml of N,O-bistrimethylsilylacetamide, dropwise, at 0°, and the mixture is stirred for 20 hours at room temperature. The heading compound, m.p. 170° (decomp.) is obtained by extraction in aqueous potassium bicarbonate solution and acidification to pH 2.

EXAMPLE 29

7-[[(3-Azidopyrazolyl-5)methoxyimino]acetylamino]-cephalosporanic acid (process a)

The heading compound, m.p. 170° (decomp.), is obtained in manner analogous to that described in Example 28 from 420 mg of (3-azidopyrazolyl-5)methoxyiminoacetic acid and 500 mg of 7-aminocephalosporanic acid.

EXAMPLE 30

7-[[(Pyrazolyl-3)hydroxyimino]acetylamino]cephalosporanic acid (process b)

1 g of 7-[[(Pyrazolyl-3)benzyloxyimino]acetylamino]-cephalosporanic acid is suspended in 20 ml of water and titrated to pH 7 with 0.1N NaOH. The resulting solution is stirred over 200 mg of 10% Pd/C in a hydrogen atmosphere for 30 hours. Filtration of the catalyst and freeze drying of the filtrate yields the heading compound, m.p.>80° (decomp.).

EXAMPLE 31

7-[[Pyrazolyl-3)carboxymethoxyimino]acetylamino]-cephalosporanic acid (process c)

100 mg of 7-[[(Pyrazolyl-3)carbamoylmethoxyimino]acetylamino]cephalosporanic acid are dissolved in 2 ml of acetic acid and 2 ml of 1N sulphuric acid and mixed at 0° with a solution of 50 mg of NaNO$_2$ in 2 ml of water. After 1 hour at room temperature, the mixture is distributed between 10 ml of water and 50 ml of a 1:1 mixture of n-butanol and ethyl acetate. The aqueous phase is extracted 5 times with the same solvent mixture and the purified organic extracts are washed with saturated sodium chloride solution and evaporated to dryness. Rubbing of the residue with ether yields the heading compound.

EXAMPLE 32

7-[[(3-Carboxypyrazolyl-5)methoxyimino]acetylamino]cephalosporanic acid (process c)

100 mg of 7-[[(3-Carbamoylpyrazolyl-5)methoxyimino]acetylamino]cephalosporanic acid are dissolved in 2 ml of acetic acid and 2 ml of 1N sulphuric acid and the solution is mixed with a solution of 50 mg of NaNO$_2$ in 2 ml of water at 0°. After 1 hour at 0° the mixture is distributed between 10 ml of water and 50 ml of a 1:1 mixture of ethyl acetate and n-butanol. The organic phase is washed several times with saturated sodium chloride solution, dried and evaporated to dryness.

EXAMPLE 33

7-[[(3-Aminopyrazolyl-5)methoxyimino]acetylamino]-3-desacetoxy-3-(1-methyltetrazolyl-5-thio)cephalosporanic acid (process d)

300 mg of 7-[[(3-Azidopyrazolyl-5)methoxyimino]acetylamino]-3-desacetoxy-3-(1-methyltetrazolyl-5-thio)cephalosporanic acid are suspended in 55 ml of water and titrated to pH 7 with 0.1N NaOH. After addition of some palladium oxide the mixture is stirred under a hydrogen atmosphere at room temperature for 1 hour. After filtration of the catalyst and freeze drying of the filtrate, the sodium salt form of the heading compound is obtained, m.p. 110°. (decomp.).

EXAMPLE 34

7-[[(3-Aminopyrazolyl-5)methoxyimino]acetylamino]-cephalosporanic acid (process d)

The sodium salt of the heading compound, m.p. 105°–120° (decomp). is obtained in manner analogous to that described in Example 33, employing 7-[[(3-azidopyrazolyl-5)methoxyimino]acetylamino]cephalosporanic acid.

EXAMPLE 35

7-[[(3-Aminopyrazolyl-5)methoxyimino]acetylamino]-3-desacetoxy-3-(1-methyltetrazolyl-5-thio)-cephalosporanic acid (process d)

300 mg of 7[[(3-Benzyloxycarbonylaminopyrazolyl-5)methoxyimino]-acetylamino]-3-desacetoxy-3-(1-methyltetrazolyl-5-thio)cephalosporanic acid are suspended in 20 ml of water and titrated to pH 7 with 0.1N NaOH. The solution is stirred over 100 mg of 10% Pd/C under a hydrogen atmosphere. Filtration of the catalyst, freeze drying of the filtrate yield the heading compound in sodium salt form, m.p. 110° (decomp.).

EXAMPLE 36

7-[[(Pyrazolyl-3)methoxyimino]acetylamino]-3-desacetoxy-3-(1-methyltetrazolyl-5-thio)cephalosporanic acid-trimethylacetoxymethyl ester 5 g of the sodium salt of 7-[[(pyrazolyl-3)methoxyimino]acetylamino]-3-desacetoxy-3-(1-methyltetrazolyl-5-thio)cephalosporanic acid are suspended in 30 ml of dry dimethylformamide and added, dropwise, at 0°, to a solution of 2.5 g of pivalic acid iodomethyl ester in 5 ml of dry dimethylformamide. After 20 minutes stirring at room temperature, the reaction mixture is distributed between 200 ml of water and 150 ml of ethyl acetate, the organic phase is washed twice with water and once with saturated sodium chloride solution, dried over magnesium sulphate and evaporated. Chromatography on silica gel (eluant: chloroform/methanol 9:1) yields the heading compound. NMR (CDCl$_3$): 1,2 (s,9H); 3.45 (ABq, 2H); 3.9 (s, 3H); 4.1 (s, 3H); 4,4 (ABq, 2H); 5.05 (d, 1H); 6.65 (d, 1H); 7.55 (d, 1H).

In manner analogous to that described in Example 36, employing appropriate starting materials in approximately equivalent amounts, the compounds of formula I, indicated in the following Table may be obtained.

| Ex. | R$_1$ | R$_2$ | R$_3$ | R$_4$ | M.P. |
|---|---|---|---|---|---|
| 37 | —CH$_3$ | —CH$_2$COCH$_2$COOC$_2$H$_5$ | 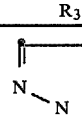 | | |
| 38 | —CH$_2$CONH$_2$ | —CH$_2$OCOC(CH$_3$)$_3$ | " | —O.CO.CH$_3$ | >90° (decomp.) |

| Ex. | R₁ | R₂ | R₃ | R₄ | M.P. |
|---|---|---|---|---|---|
| 39 | " | " | " | 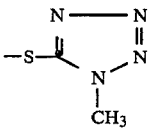 | >100° (decomp.) |
| 40 | —CH₂COOC₂H₅ | " | " | " | 95–110° (decomp.) |

EXAMPLE 41

7-[[(Pyrazolyl-3)-methoximino]acetylamino]-3-desacetoxy-3-(1-methyltetrazolyl-5-thio)-cephalosporanic acid, syn and anti forms 250 g of Lichroprep ®RP8 40–63 μm (Fa. Merck) are filled, dry, in a medium pressure glass column (Lit.: H. Libner and G. Seidl, Chromatographia, p.600 [1979]). The column is washed with acetonitrile and finally conditioned with acetonitrile/water (25:75). 2 g of a crude isomer mixture of 7-[[(pyrazolyl-3)-methoxyimino]acetylamino]-3-desacetoxy-3-(1-methyltetrazolyl-5-thio)cephalosporanic acid, consisting of 47% of syn- and 23% of anti-isomer, as well as unidentified impurities, are dissolved in 35 ml of acetonitrile/water (1:1) and added to the column. The column is eluted with acetonitrile/water (25:75) (flow rate about 40 ml/minute at 5 bar) and fractions of approximately 20 ml are collected. The fractions are checked by a thin layer chromatography on RP12 plates using acetonitrile/water (25:75) as eluant. Uniform fractions are purified and lyophilysed to obtain 0.7 g of the syn-isomer and 0.55 g of the anti-isomer.

Syn-isomer: m.p. 146°–148° (decomp.); $[\alpha]_D^{20}$ (Na-salt) = −23° (c = 1.14 g/100 ml H₂O): Rf = 0.60 (RP12-Plates, CH₃CN:H₂O = 25:75); ¹H-NMR (90 MHZ, Na-salt in D₂O): 7.80 (1H,d,J = 1 Hz); 6.72 (1H,d,J = 1 Hz); 5.80 (1H,d,J = 2.5 Hz); 5.19 (1H,d,J = 2.5 Hz); 4.33 (1H,d,J = 6 Hz); 4.09 (1H,d,J = 6 Hz); 4.02 (6H,s); 3.80 (1H,d,J = 9 Hz); 3.43 (1H,d,J = 9 Hz).

Anti-Isomer: m.p. 146°–148° (decomp.). $[\alpha]_D^{20}$ (Na-salt) = 4° (c = 1.19 g/100 ml H₂O): Rf = 0.48 (RP12-plates, CH₃CN:H₂O = 25:75); ¹H-NMR (90 MHZ, Na-Salt in D₂O): 7.80 (1H,d,J = 1 Hz); 6.95 (1H,d,J = 1 Hz); 5.73 (1H,d,J = 2,5 Hz); 5.17 (1H,d,J = 2.5 Hz); 4.35 (1H,d,J = 6 Hz); 4.13 (3H,s); 4.02 (3H,s); 3.80 (1H,d,J = 9 Hz); 3.43 (1H,d,J = 9 Hz).

EXAMPLE 42

7-[[(Pyrazolyl-3)-methoxyimino]acetylamino]cephalosporanic acid, syn and anti forms In manner analogous to Ex. 41, the following isomers may be obtained:

Syn-Isomer: m.p. 110°–115° (decomp.): ¹H-NMR (free acid in DMSO-d₆): 9.4 (1H,d,J = 4 Hz); 7.71 (1H,d,J = 1,5 Hz); 6.5 (1H,d,J = 1.5 Hz); 5.82 (1H,dd,J₁ = 4 Hz, J₂ = 3 Hz); 5.15 (1H,d,J = 3 Hz); 5.02 (1H,d,J = 6 Hz); 4.72 (1H,d,J = 6 Hz); 3.89 (3H,2); 2.03 (3H,s).

Anti-isomer: m.p. 110°–115° (decomp.): ¹H-NMR (free acid in DMSO-d₆): 9.22 (1H,d,J = 4 Hz); 7.71 (1H,d,J = 1.5 Hz); 6.82 (1H,d,J = 1.5 Hz); 5.80 (1H,dd,J₁ = 4 Hz, J₂ = 3 Hz); 5.20 (1H,d,J = 3 Hz); 5.02 (1H,d,J = 6 Hz); 4.72 (1H,d,J = 6 Hz); 4.03 (3H,s); 2.03 (3H,s).

EXAMPLE 43

7-[[(Pyrazolyl-3-)-syn-methoxyimino]acetylamino]-3-desacetoxy-3-(1-methyltetrazolyl-5-thio)-cephalosporanic acid 1250 mg of a syn/anti-mixture of 7-[[(pyrazolyl-3)methoxyimino]-acetylamino]-3-desacetoxy-3-(1-methyltetrazolyl-5-thio)cephalosporanic acid (containing 76% of the syn- and 20% of the anti-isomer) are dissolved in 100 ml of phosphate buffer and incubated with 1 ml of a β-lactamase enzyme solution at 30°. Every hour during incubation 25 μl probes are taken and investigated by HPLC. After 5 hours, the mixture is frozen and lyophilysed. The lyophilysate is taken up in 50 ml of water, layered with 200 ml of ethyl acetate and acidified to pH 1 with conc. hydrochloric acid. After separation of the ethyl acetate phase, the aqueous phase is extracted 5 times each with 100 ml of ethyl acetate. The purified ethyl acetate extracts are washed with water and sodium chloride solution, dried with sodium sulphate and evaporated to dryness in vacuo. The residue is rubbed with 20 ml of diisopropylether. Filtration yields the heading compound as free acid, which according to HPLC-analysis contains 89% of the syn-isomer, 1.5% of the anti-isomer and polar impurities of unidentified natures.

The β-lactamase enzyme solution can for example be produced as follows: 100 ml of an overnight culture of E. coli 640 are added to 2 liters of TSB and cultivated, with shaking at 37°, to an optical density of 0.8 at 600 nm. The culture is centrifuged at 20° (Sorvall GS3-Rotor, 9000 Rpm, 20 minutes), washed twice, each time with 200 ml of a solution using 10 mM Tris-HCl and 30 nM NaCl (pH 7.3), and centrifuged again (as above). After suspension in 1000 ml of a solution of 20% saccharose, 3 mM EDTA, 33 mM Tris.HCl (pH 7.3), the mixture is stirred for 10 minutes at 20° and centrifuged again (Sorvall SS 34 Rotor, 11.500 Upm, 5 minutes). The following procedure is effected at 4°: the cells are suspended in 20 ml of a 0.5M solution of MgCl₂ and stirred for 10 minutes. After centrifugation (Sorvall SS 34 Rotor, 14.700 Upm, 10 minutes) the supernatant is frozen in portions of each 1 ml.

Determination of Enzyme Activity 0.25 ml of the above-obtained supernatant are added to a 0.025 mM solution of NITROCEFIN in 1 ml of phosphate buffer (pH 7.0). Thereby results an initial change of the optical density of 0.049 minutes at 486 nm.

Starting materials employed in the foregoing Examples may be obtained as follows:

(A) (Pyrazolyl-3)methoxyimino acetic acid (for Examples 2, 8, 9, 14, 23, 24, 35 to 42)

(a) (β-Dimethylaminoacryloyl)methoxyiminoacetic acid methyl ester 212.4 g of α-Methoxyiminoacetoacetic acid methyl ester and 390 ml of N,N-dimethylformamide-dimethylacetal are boiled under reflux in 300 ml of benzene for 10 hours. After cooling, the mixture is evaporated to dryness and a dark residue is recrystallised from ethanol to obtain yellow crystals of the heading compound, m.p. 63°–64°.

(b) (Pyrazolyl-3)methoxyiminoacetic acid methyl ester 21.4 g of β-dimethylaminoacryloyl)methoxyimino acetic acid methyl ester are suspended at room temperature in 200 ml of water and, after addition of 20 g of hydrazine monohydrochloride and 20 ml of 2-propanol, boiled for 30 minutes. The heading compound, crystallises on cooling m.p. 70°.

(c) (Pyrazolyl-3)methoxyiminoacetic acid 38.8 g of (Pyrazolyl-3)methoxyimino acetic acid methyl ester are warmed in 100 ml of ethanol/50 ml of 4N NaOH for 3 hours at 90°. After cooling to 0°, the mixture is acidified to pH 1 with conc. hydrochloric acid and concentrated to about 20 ml. The resulting precipitate is recrystallised from 100 ml of water to obtain the heading compound in the form of a syn/anti mixture (4:1), m.p. 150°.

(B) (1-Methylpyrazolyl-3)methoxyiminoacetic acid (for Example 15)

(a) (Pyrazolyl-3)methoxyiminoacetic acid ethyl ester

The heading compound may be obtained as a colourless oil in manner described under (A) above.

(b) (1-Methylpyrazolyl-3)methoxyiminoacetic acid ethyl ester

To a suspension of 1.65 g of NaH in 20 ml of absolute tetrahydrofuran is added at 0° a solution of (pyrazolyl-3)methoxyiminoacetic acid ethyl ester in 200 ml of tetrahydrofuran. After hydrogen evolution ceases, 9.5 ml of methyl iodide are added dropwise and the mixture is stirred for 20 hours at room temperature. The mixture is evaporated and the residue is divided between 200 ml of ethyl acetate and water to yield after evaporation of the organic phase the heading compound as a colourless oil.

NMR (CDCl$_3$); 1.3 (t, 3H); 3.85 (s, 3H); 3.90 (s, 3H); 6.45 (d, 1H); 7.65 (d, 1H).

(c) (1-Methylpyrazolyl-3)methoxyiminoacetic acid 3.2 g of (1-methylpyrazolyl-3)methoxyimino acetic acid ethyl ester and 720 mg of lithium hydroxide are stirred in 30 ml of water for 18 hours at room temperature. The mixture is acidified to pH 1 with conc. hydrochloric acid and the product filtered off to obtain the heading compound, m.p. 160°–162°.

(C) [(Pyrazolyl-3)carbethoxymethoxyimino]acetic acid (for Example 3)

(a) 2-Hydroxyiminoacetoacetic acid-tert. butylester

To a mixture of 158 g of acetoacetic acid-tert. butylester and 1000 ml of glacial acetic acid is added dropwise, while maintaining the temperature at 5°, a solution of 86.4 g of NaNO$_2$ in 500 ml of water. After 4 hours stirring at 5°, the mixture is extracted 5 times with ether, the purified ether extracts are washed 5 times with water and twice with saturated sodium chloride and evaporated to dryness to obtain the heading compound, m.p. 55°–63°.

(b) 2-Methoxyiminoacetoacetic acid-tert.-butyl ester

To a solution of 215 g of Na$_2$CO$_2$ in 2200 ml of water is added at room temperature a solution of 128 g of 2-hydroxyiminoacetoacetic acid-tert.butyl ester in 475 ml of methanol. 255 g of dimethyl sulphate are added, dropwise, at 8°–10°, and after 3 hours at 8°–10° and 15 hours at room temperature, the mixture is filtered. The filtrate is extracted 3 times with ethyl acetate extracted 3 times with ethyl acetate, dried over magnesium sulphate and evaporated to obtain the heading compound.

NMR (CDCl$_3$): 1.55 (s, 9H); 2.3 (s, 3H); 4.0 (s, 3H).

(c) 2-(1-Methyl-1-methoxy)ethoxyimino acetoacetic acid-tert.-butyl ester

To a solution of 187 g of 2-methoxyimino acetoacetic acid-tert.-butyl ester in 200 ml of dichloromethane is added 2 g of a strong acid ion exchanger. 200 ml of isopropanylmethyl ether are added with ice cooling, dropwise. After 18 hours at room temperature the ion exchanger is filtered off and the mixture is evaporated to dryness. The resulting oil is used in the ext step without further purification.

NMR (CDCl$_3$): 1.55 (s, 15H); 2.4 (s, 3H); 3.3 (s, 3H).

(d) 4-Dimethylaminomethylene-2-(1-methyl-1-methoxy)ethoxyiminoacetoacetic acid-tert.-butylester 255 g of 2-(1-methyl-1-methoxy)ethoxyimino acetoacetic acid tert.-butylester and 280 ml of N,N-dimethylformamidedimethylacetal are heated to boiling in 300 ml of toluol for 3 hours. The mixture is cooled to 0° and the precipitate is filtered off to obtain the heading compound, m.p. 85°–89°.

(e) (Pyrazolyl-3) (1-methyl-1-methoxy)ethoxyiminoacetic acid-tert.-butyl ester To a solution of 215 g of 4-dimethylaminomethylene -2-(1-methyl-1-methoxy)ethoxyiminoacetoacetic acid tert.-butylester in 1500 ml of methanol is added a mixture of 70 g of acetic acid and 35 g of hydrazine hydrate. After 50 hours at room temperature, the mixture is evaporated to dryness, the residue is taken up in 1500 ml of ethyl acetate. The mixture is washed with saturated sodium bicarbonate solution and evaporated to dryness to obtain the heading compound, m.p. 102°–106°.

(f) (Pyrazolyl-3)hydroxyiminoacetic acid-tert.-butylester 173 g of (Pyrazolyl-3) (1-methyl-1-methoxy)ethoxyiminoacetic acid-tert.-butylester are stirred in 1500 ml over 2 g of a strong acid ion exchange resin for 8 hours at room temperature. After filtration and evaporation to dryness the residue is rubbed with petroleum ether, to obtain the heading compound, m.p. 152°–159°.

(g) [(Pyrazolyl-3)carbethoxymethoxyimino]acetic acid-tert.-butylester

To a solution of 24 g of (pyrazolyl-3)hydroxyiminoacetic acid tert.-butylester and 17 g of bromoacetic acid ethyl ester in 100 ml of dichloromethane is added dropwise, at room temperature, slowly, a solution of 15 g of 1,5-diazobicyclo[5,4,0]undec-5-en in 50 ml of dichloromethane. After 24 hours at room temperature, the mixture is evaporated to dryness, the residue is distributed between ethyl acetate and 1N HCl and the concentrated residue of the ethyl acetate is chromatographed over silica gel to obtain the heading compound, m.p. 84°–85°.

(h) [(Pyrazolyl-3)carbethoxymethoxyimino]acetic acid 2.4 g [(Pyrazolyl-3)carbethoxymethoxyimino]acetic acid-tert.-butylester are stirred in 20 ml of trifluoroacetic acid for 30 minutes at room temperature. The mixture is evaporated to dryness in vacuo, the residue is taken up in toluene, and the mixture is evaporated to dryness. The residue is rubbed with ether to obtain the heading compound, m.p. 124°–129°.

(D) [(Pyrazolyl-3)carbamoylmethoxyimino]acetic acid (for Example 4)

(a) [(Pyrazolyl-3)carbamoylmethoxyimino]acetic acid-tert.-butylester (a) 5 g [(Pyrazolyl-3)carbethoxymethoxyimino]acetic acid-tert.-butylester are stirred in 200 ml of a solution of ammonia in methanol for 24 hours at room temperature. After evaporation to dryness, the heading compound is obtained by rubbing with ether, m.p. 112°–118°.

(b) [(Pyrazolyl-3)carbamoylmethoxyimino]acetic acid 2 g [(Pyrazolyl-3)carbamoylmethoxyimino]acetic acid-tert.-butylester are reacted in manner analogous to that described above under C/h, to obtain the heading compound, m.p. 155°–159°.

(E) [(Pyrazolyl-3)cyanomethoxyimino]acetic acid (for Example 5)

(a) [(Pyrazolyl-3)cyanomethoxyimino]acetic acid-tert.-butylester

To a solution 2 g of [(pyrazolyl-3)carbamoylmethoxyimino]acetic acid-tert.-butylester in 100 ml of absolute toluene and 5 ml of triethylamine is added at room temperature with stirring in small portions 2 g of phosphorous pentoxide. The mixture is heated for 3 hours at 80°, cooled to 0°, and divided between 100 ml of ethyl acetate, and 50 ml of ice water. The organic phase is evaporated and the residue is chromatographed over silica gel. The heading compound results as a colourless oil. NMR (CDCl$_3$): 1.5 (s, 9H); 4.65 (s, 2H); 6.6 (d, 1H); 7.5 (d, 1H).

(b) [(Pyrazolyl-3)cyanomethoxyimino]acetic acid 550 mg of [(pyrazolyl-3)cyanomethoxyimino]acetic acid-tert.-butyl ester are reacted in manner analogous to that described under C/h, to obtain the heading compound, m.p. 182°–186°.

(F) (Pyrazolyl-3)benzyloxyiminoacetic acid (for Example 6)

(a) (Pyrazolyl-3)benzyloxyiminoacetic acid-tert.-butylester 2.11 g of (Pyrazolyl-3)hydroxyiminoacetic acid tert.-butyl ester and 1.71 g of benzylbromide are stirred for 16 hours at room temperature in a mixture of 1.38 g of K$_2$CO$_3$ in 10 ml of water and 100 ml of acetone. Evaporation to dryness and distribution of the residue between 100 ml of ether and water yields the heading compound. NMR (CDCl$_3$): 1.6 (s, 9H); 5.25 (s, 2H); 6.55 (d, 1H); 7.3 (s, 5H); 7.5 (d, 1H).

(b) (Pyrazolyl-3)benzyloxyiminoacetic acid 2 g of (Pyrazolyl-3)benzyloxyiminoacetic acid-tert.-butylester are reacted in manner analogous to that of C/h above, to obtain the heading compound, m.p. 126°–128°.

(G) [(Pyrazolyl-3)methoxymethoxyimino]acetic acid (for Example 7)

(a) 2-(Methoxymethoxyimino)acetoacetic acid methyl ester

To a suspension of 4.13 g of 80% NaH in 50 ml of dry tetrahydrofuran are added successively at 0° 18.14 g of 2-hydroxyiminoacetoacetic acid methyl ester and 9 g of chloromethylmethylether. After 30 minutes at room temperature, the mixture is divided between 200 ml of ethyl acetate and acqueous buffer (pH 5.5). The contents of the ethyl acetate phase are bulb distilled to obtain the heading compound, m.p. 115°–120°/0.1 Torr.

(b) 4-Dimethylaminomethylene-2-(methoxymethoxyimino)acetoacetic acid methyl ester 6.4 g of 2-(methoxymethoxyimino)acetoacetic acid methyl ester in 30 of toluene are heated with 9 ml of N,N-dimethylformamidedimethylacetal for 5 hours at boiling. After cooling, the semi-crystalline residue is dissolved by heating in diisopropylether, the mixture is filtered. The precipitate obtained after cooling is filtered and dried to obtain the heading compound, m.p. 99°–100°.

(c) [(Pyrazolyl-3)methoxymethoxyimino]acetic acid methyl ester

To a mixture of 0.6 ml of hydrazine hydrate (100%) and 1.2 ml of the glacial acetic acid in 50 ml of methanol is added at room temperature, with stirring, 2.5 g of 4-dimethylaminomethylene-2-(methoxymethoxyimino)acetoacetic acid methyl ester. After 3 days at room temperature, the mixture is evaporated in vacuo, and the residue is distributed between ethyl acetate and aqueous sodium bicarbonate solution. The organic phase is evaporated to dryness and the residue is rubbed with petroleum benzene to obtain the heading compound, m.p. 87°–89°.

(d) [(Pyrazolyl-3)methoxymethoxyimino]acetic acid 20 g of [(Pyrazolyl-3)methoxymethoxyimino]acetic acid methyl ester and 4.6 g of LiOH are stirred in 60 ml of water for 30 minutes at 80°. After cooling, the pH is adjusted to 1.5 by addition of a strongly acidic ion exchange resin. The mixture is filtered and the filtrate is freeze dried. The heading compound is obtained as an amorphous, colourless powder.

NMR (DMSO$_{d6}$/CDCl$_3$): 3,3 (s, 3H); 5.1 (s, 2H); 6.5 (d, 1H); 7.6 (d, 1H).

(H) (3-Carbamoylpyrazolyl-5)methoxyimino acetic acid (for Example 10)

(a) 4-Carbethoxycarbonyl-2-(methoxyimino acetoacetic acid-tert.-butylester

To a solution of 5.75 g of sodium in 500 ml of absolute ethanol is added, dropwise, with stirring, and in the absence of moisture, at 0° a solution of 50.4 g of 2-(methoxyimino)acetoacetic acid-tert.-butyl ester and 33.8 g of oxalic acid diethylester in 50 ml of dry ether. After 50 hours at room temperature the mixture is evaporated to dryness, the residue is taken up in 100 ml of water, and the mixture is acidified to pH 5 with 1N HCl. Ethyl acetate extraction and silica gel chromatography of the resulting crude product yields the heading compound as a yellow oil.

(b) (3-Carbethoxypyrazolyl-5)methoxyiminoacetic acid tert.-butyl ester

To a solution of 10 g of 4-carbethoxycarbonyl-2-(methoxyimino)acetoacetic acid-tert.-butyl ester in 70 ml of methanol and 4 ml of acetic acid are added, dropwise, at room temperature, with stirring, 3.4 ml of 100% hydrazine hydrate. The mixture is allowed to stand for 30 hours at room temperature and evaporated to dryness. The residue is distributed between 100 ml of ethyl acetate and 50 ml of 1N HCl. The content of the organic phase is chromatographed on silica gel to obtain the heading compound as a colourless oil.

NMR (CDCl$_3$): 1.3 (t, 8 Hz, 3H); 1.6 (s, 9H); 3.95 (s, 3H); 4.3 (q, 8 Hz, 2H); 6.9 (s, 1H).

(3-Carbethoxypyrazolyl-5)-methoxyiminoacetic acid may be obtained by splitting the trifluoroacetic acid, m.p. 146°–148°.

(c) (3-Carbamoylpyrazolyl-5)methoxyiminoacetic acid-tert.-butylester 10 g of (3-carbethoxypyrazolyl-5)methoxyiminoacetic acid-tert.-butylester are stirred in 100 ml of a solution of ammonia in methanol for 6 days. After evaporation to dryness the oily residue is crystallised by rubbing with a mixture of cyclohexane in diisopropylether to obtain the heading compound, m.p. 104°–107°.

(d) (3-Carbamoylpyrazolyl-5)methoxyiminoacetic acid 1 g of (3-Carbamoylpyrazolyl-5)methoxyiminoacetic acid-tert.-butylester are reacted in manner analogous to that under C/h above, to obtain the heading compound above, m.p. 217° (decomp.).

(I) (1-Phenylpyrazolyl-5)methoxyimino acetic acid (for Example 11)

22.7 g of (3-Dimethylaminoacryloyl)methoxyimino acetic acid ethyl ester and 14.5 g of phenyl hydrazine HCl are heated at boiling in 200 ml of methanol for 3 hours. The mixture is evaporated to dryness in vacuo and the residue is distributed between water and chloroform. Evaporation to dryness of the chloroform phase yields a yellow oil. This product is heated to boiling with 4 g of lithium hydroxide in 200 ml of water. After cooling, the mixture is acidified to pH 1 with conc. HCl. The precipitate is filtered off, washed with water and dried to obtain the heading compound, m.p. 124°–128°.

(J) (3-Benzyloxycarbonylaminopyrazolyl-5)-methoxyimino acetic acid (for Example 12)

(a) (3-Hydrazinocarbonylpyrazolol-5)methoxyimino acetic acid-tert.-butyl ester 4.11 g of (3-carbethoxypyrazolyl-5)methoxyimino acetic acid tert.-butyl ester and 1 ml of hydrazine hydrate are heated in 20 ml of ethanol for 20 hours, at boiling. After evaporation to dryness, the residue is chromatographed on silica gel to obtain the heading compound, m.p. 180° (decomp.).

(b) (3-Benzyloxycarbonylaminopyrazolyl-5)methoxyimino acetic acid tert.-butylester 1 g of (3-Hydrazinocarbonylpyrazolyl-5)methoxyimino acetic acid tert.-butyl ester are dissolved in 10 ml of 1N HCl with toluene; a solution of 250 mg NaNO$_2$ in 2 ml of water is added, dropwise, at 0°, and the mixture is stirred for 30 minutes. The phases are separated, and the toluene phase is dried well with K$_2$CO$_3$. After addition of 1 ml of benzyl alcohol, the mixture is warmed to 90° and, after 1 hour, evaporated to dryness. The residue is chromatographed on silica gel to obtain the heading compound as a colourless oil.

NMR (CDCl$_3$): 1,6 (s, 9H); 3.9 (s, 3H); 5.1 (s, 2H); 6.5 (s, 1H); 7.2 (s, 5H).

(c) (3-Benzyloxycarbonylaminopyrazolyl-5)methoxyimino acetic acid 520 g of (3-benzyloxycarbonylaminopyrazolyl-5)methoxyimino acetic acid-ter.-butyl ester are reacted in manner analogous to that of C/h above to obtain the heading compound, m.p. 157°–160°.

(K) (3-Methylmercaptopyrazolyl-5)methoxyimino acetic acid (for Example 13)

(a) (3-Methylmercaptopyrazolyl-5)methoxyimino acetic acid ethyl ester 13.85 g of 2-Methoxyimino-3-oxo-5,5-bis-methylmercaptopent-4-en-carboxylic acid ethyl ester in 150 ml of N-butanol are boiled for 30 minutes with 5.7 ml of glacial acetic acid and 4.9 ml of hydrazine hydrate. After cooling, the mixture is distributed between 200 ml of ethyl acetate and saturated aqueous sodium bicarbonate solution and the content of the organic phase is chromatographed on neutral aluminium oxide to obtain the heading compound, m.p. 77°–80°.

(b) (3-Methylmercaptopyrazolyl-5)methoxyimino acetic acid 7 g of (3-methylmercaptopyrazolyl-5)methoxyimino acetic acid ethyl ester are warmed in 20 ml of ethanol and 50 ml of 10% sodium hydroxide for 3 hours at 80°. After cooling, the mixture is extracted with ethyl acetate and the aqueous phase is acidified to pH 1.5 by addition of a strongly acidic ion exchange. After filtration of the ion exchange resin, the filtrate is freeze dried and the residue is rubbed with ether to obtain the heading compound, m.p. 146°–153°.

(L) (3-Azidopyrazolyl-5)methoxyimino acetic acid (for Examples 28 and 29)

(a) 2-Methoxyimino-3-oxo-5,5-bis-methylmercapto-4-pentenecarboxylic acid ethyl ester 11.9 g of NaH are suspended in 500 ml of dry tetrahydrofuran and the mixture is heated to boiling with stirring. To the boiling suspension is added one-third of a solution of 25.1 ml of methyl iodide and 34.6 g of 2-methoxyiminoaceto acetic acid ethyl ester in 13 ml of carbon disulphide. After the reaction begins (1–3 hours), the remainder of the solution is slowly added, dropwise. The mixture is stirred overnight at room temperature and evaporated to dryness. The residue is distributed between 500 ml of ether and a mixture of 250 ml of water and 250 g of ice. The organic phase is washed with water, dried, and concentrated to remove the solvent to obtain the heading compound, 80°–83°.

(b) 2-Methoxyimino-3-oxo-5-[N-(tert.-butoxycarbonylhdrazono]-5-methylmercaptopentane carboxylic acid ethyl ester A mixture of 1.38 g of 2-methoxyimino-3-oxo-5,5-bis-mercaptomethyl-4-pentenecarboxylic acid ethyl ester, 6.6 g of tert.-butylcarbazate, 1.5 g of acetic acid and 100 ml of n-butanol are heated at reflux for 90 minutes. The mixture is concentrated under high vacuum ($10^{-2}$ Torr) at 50°–60° bath temperature. The resulting oily residue is distributed 3 times against ethyl acetate/0.1N HCl, and then against NaHCO$_3$. The remaining organic phase is dried with MgSO$_4$ and is concentrated on a rotary evaporator. The residue is chromatographed over silica with dichloromethane to obtain the heading compound in the form of an oil.

NMR (CDCl$_2$): 1.27 (t, 3H); 1.5 (s, 9H); 2.5 (s, 3H); 3.35 (q, 2H); 3.9, (s, 3H); 4.2 (q, 2H).

(c) 3-[(2-N-tert.-butoxycarbonyl)hydrazinopyrazolyl-5]methoxyimino acetic acid ethyl ester (syn)

A mixture of 360 mg of 2-methoxyimino-3-oxo-5-[(N-tert.-butoxycarbonyl)hydrazono]-5-methylmercaptopentane carboxylic acid ethyl ester, 120 mg of acetic acid, 100 mg of hydrazine hydrate and 10 ml of n-butanol is maintained at reflux for 60 minutes. The reaction mixture is concentrated at $10^{-2}$ Torr and a bath temperature of approx. 40°–50°. The residue is taken up in ethyl acetate and distributed 3 to 4 times in 0.1N HCl and then against aqueous NaHCO$_3$ (about 10%). The resulting organic phase is dried with magnesium sulphate and evaporated to yield a crystalline residue, which is washed once to twice on glass chips with dichloromethane to obtain the heading compound, 150°–151°.

(d) (3-Hydrazinopyrazolyl-5)methoxyimino acetic acid ethyl ester (syn)

220 mg of 3-[(2-N-tert.-butoxycarbonyl)hydrazinopyrazolyl-5]methoxyimino acetic acid ethyl ester are introduced at 0° into 5 ml of trifluoroacetic acid and the mixture is maintained at room temperature for 30 minutes. The mixture is evaporated in vacuo (12 Torr/20° bath temperature) and the residue is taken up in ethyl acetate and distributed twice against aqueous sodium bicarbonate. The organic phase is dried with MgSO$_4$ and then evaporated in vacuo (12 Torr/20° bath temperature) to obtain the heading compound.

NMR (CDCl$_3$): 1.37 (t, 3H); 3.95 (s, 3H); 4.35 (q, 2H); 5.46 (sb, 4H); 5.78 (s, 1H).

By alkaline hydrolysis, (3-hydrazinopyrazolyl-5)methoxyimino acetic acid may be obtained (for Example 21).

(e) (3-Azidopyrazolyl-5)methoxyimino acetic acid ethyl ester (syn)

347 mg (3-Hydrazinopyrazolyl-5)methoxyimino acetic acid ethyl ester are dissolved in 20 ml of 1N HCl and mixed at 0° with 130 mg of NaNO$_2$ in 30 ml of water. After 30 minutes reaction time, the mixture is diluted with 100 ml of water, extracted three times with ethyl acetate and the organic phase washed with aqueous sodium bicarbonate and dried with MgSO$_4$. After evaporation in vacuo (12 Torr/20° bath temperature) the crystalline heading compound remains, m.p. 61°–63°.

(f) (3-Azidopyrazolyl-5)methoxyimino acetic acid (syn)

5 g of (3-Azidopyrazolyl-5)methoxyimino acetic acid ethyl ester and 1.7 g of lithium hydroxide are stirred in 150 ml of water for 20 hours at room temperature. After filtration of a little insoluble material, the pH is adjusted to pH 1 with conc. HCl and the resulting precipitate is washed with water and dried to obtain the heading compound, m.p. 155°–157°.

(M) (1-Methylpyrazolyl-5)methoxyimino acetic acid (for Examples 1, 16)

15 g of Monomethylhydrazine, 29.5 g of oxalic acid and 35 g of (β-dimethylaminoacryloyl)methoxyimino acetic acid methyl ester are boiled for 30 minutes in 500 ml of methanol. After cooling and evaporation to dryness, the residue is divided between ether and saturated sodium chloride solution and the ether phase is evaporated. The residual oil is chromatographed on 2.5 kg of silica gel to obtain (1-methylpyrazolyl-5)methoxyimino acetic acid methyl ester (colourless oil).

NMR (CDCl$_3$, ppm in δ): 7.42 (d, 1.8 Hz); 6.32 (d, 1.8 Hz, 1H); 4.08 (s, 3H, NCH$_3$); 4.02 (s, 3H, NOCH$_3$); 3.91 (s, 3H, COOCH$_3$).

Also obtained is (1-methylpyrazolyl-3)acetic acid methyl ester, m.p. 160°–165°.

NMR (CDCl$_3$, ppm in δ): 7.33 (d, 2.5 Hz, 1H); 6.57 (d, 2.5 Hz, 1H); 3.99 (s, 3H, NOCH$_3$); 3.94 (s, 3H, COOCH$_3$); 3.88 (s, 3H, NCH$_3$).

Alkaline hydrolysis of this yields (1-methylpyrazolyl-5)methoxyimino acetic acid, m.p. 155°–158°.

(N) (3-Furylidenehydrazinopyrazolyl-5)methoxyiminoacetic acid (for Example 17)

A solution of 2.27 g of (3-hydrazinopyrazolyl-5)methoxyimino acetic acid ethyl ester and 15 g of sodium acetate in 100 ml of 50% ethanol is mixed with 960 mg of Furfural. After 20 minutes, the mixture is evaporated in vacuo, and the residue is mixed with water and the resulting crystals are filtered off to obtain the heading compound.

NMR (CDCl$_3$): 1.30 (t, 3H); 3.9 (s, 3H); 4.3 (q, 2H); 6.0 (s, 1H); 6.4 (m, 3H); 7.2 (d, 1H); 7.55 (s, 1H); 9.10 (sb, 1H).

The free acid may be obtained by alkaline hydrolysis.

(O) [3-Amino-2-(N-isobutyloxycarbonyl)pyrazolyl-5]methoxyimino acetic acid (for Example 18)

(a) (3-Aminopyrazolyl-5)methoxyimino acetic acid ethyl ester

To a solution of 100 mg of (3-azidopyrazolyl-5)methoxyimino acetic ethyl ester and 200 mg of triethylamine in 20 ml of methanol is added, dropwise, with stirring, 250 mg of propane-1,3-dithiol. After a reaction time of 5 minutes, the mixture is evaporated in vacuo and the residue is mixed with diisopropylether and filtered to obtain the heading compound.

(b) [3-Amino-pyrazolyl-5]methoxyimino acetic acid

A mixture of 1 g of (3-aminopyrazolyl-5)methoxyimino-acetic acid in ethyl ester, 40 ml of water, 5 ml of methanol and 225 ml of lithium hydroxide is stirred for 90 minutes at room temperature, is then acidified to pH 2.0 by addition of IR 120 ion exchanger and filtered. The filtrate is lyophilysed to obtain the heading compound.

NMR (CDCl$_3$/DMSO): 3.93 (s, 3H); 4.9 (sb, 4H); 5.7 (s, 1H).

(c) [3-Amino-2-(N-isobutyloxycarbonyl)pyrazolyl-5]methoxyimino acetic acid

To a mixture of 1.34 g of (3-aminopyrazolyl-5)methoxyimino acetic acid, 2.36 g of triethylamine and 60 ml of methylene dichloride is added, dropwise, at 4°, a solution of 2.19 g of chloroformic acid isobutyl ester in 10 ml of dichloromethane. After 3 hours at 4°, the mixture is extracted with water and the aqueous phase is acidified to pH 2.5 with HCl. The resulting crystals are separated to obtain the heading compound.

NMR (CDCl$_3$/DMSO): 0.90 (s, 3H); 1.0 (s, 3H); 1.0 (s, 3H); 3.90 (s, 3H); 4.15 (d, 2H); 5.55 (s, 1H); 6.05 (sb, 3H).

(P) (5-Azido-1-methylpyrazolyl-3)methoxyimino acetic acid (for Example 19)

(a) (3-Azido-1-methylpyrazolyl-5)methoxyimino acetic acid ethyl ester and
(5-Azido-1-methylpyrazolyl-3)methoxyimino acetic acid ethyl ester To a solution of 1.2 g of (3-azidopyrazolyl-5)methoxyimino acetic acid ethyl ester in 100 ml of tetrahydrofuran is added, at room temperature, 250 mg of 50% sodium hydride and after 10 minutes reaction time 5 ml of methyl iodide. After a further 20 minutes, the mixture is evaporated in vacuo, and the residue is taken up in ethyl acetate. The mixture is shaken with 0.5N HCl and once with 10% NaHCO$_3$, and then with sodium chloride solution. The organic phase is dried with MgSO$_4$ and evaporated in vacuo. The oily crystalline residue is chromatographed with dichloromethane over silica, to obtain the heading compounds.

(3-Azido-1-methylpyrazolyl-5)methoxyimino acetic acid ethyl ester, m.p. 45°:
NMR (CDCl$_3$): 1.34 (t, 3H); 3.95 (s, 3H); 4.00 (s, 3H); 4.32 (q, 2H); 5.86 (s, 1H).

(5-Azido-1-methylpyrazolyl-3)methoxyimino acetic acid ethyl ester, mp.p 106°–107°:
NMR (CDCl$_3$): 1.4 (t, 3H); 3.6 (s, 3H); 3.95 (s, 3H); 4.35 (a, 2H); 6.25 (s, 1H).

(b) (5-Azido-1-methylpyrazolyl-3)methoxyimino acetic acid

To a solution of 4 g of (5-azido-1-methylpyrazolyl-3)methoxyimino acetic acid ethyl ester in 17 ml of methanol is added a solution of 950 mg of lithium hydroxide dissolved in 130 ml of water. After 4 hours reaction time, the mixture is mixed with enough ion exchanger to bring the pH value to 2.3. The mixture is separated on glass chips and the filtrate is evaporated in vacuo to obtain the heading compound, m.p. 145°–150°.

NMR (CDCl$_3$/DMSO): 3.55 (s, 3H); 3.86 (s, 3H); 6.26 (s, 1H); 7.22 (sb, 2H).

(Q) (3-Methylsulphonylpyrazolyl-5)methoxyimino acetic acid (for Example 20)

To a solution of 1.21 g of (3-methylmercaptopyrazolyl-5)methoxyimino acetic acid ethyl ester in 40 ml of acetic acid is added, dropwise, with stirring, at room temperature, a solution of 2.6 g of KMnO$_4$ in 40 ml of water. After 40 minutes, sulphur dioxide is introduced to reduce the resulting manganese dioxide and the mixture is evaporated in vacuo. The residue is mixed with water and sodium bicarbonate and is extracted with ethyl acetate. The organic phase is dried with MgSO$_4$ and evaporated in vacuo to obtain the ethyl ester of the heading compound as an oil.

NMR (CDCl$_3$): 1.4 (t, 3H); 3.24 (s, 3H); 4.03 (s, 3H); 4.45 (a, 2H); 7.0 (s, 1H).

The free carboxylic acid may be obtained by alkaline hydrolysis thereof.

(R) (3-Azido-1-methylpyrazolyl-5)methoxyimino acetic acid (for Example 25)

To a solution of 4 g of (3-azido-1-methylpyrazolyl-5)methoxyimino acetic acid ethyl ester is added 950 mg of lithium hydroxide dissolved in 130 ml of water. After 4 hours, the mixture is mixed with enough ion exchanger to bring the pH to 2.3. The mixture is filtered over glass chips and evaporated in vacuo to obtain the heading compound, m.p. 153°–157°.

(S) (3-Amino-1-methylpyrazolyl-5)methoxyimino acetic acid (for Example 26)

(a) (3-Amino-1-methylpyrazolyl-5)methoxyimino acetic acid ethyl ester

To a solution of 4 g of (3-azido-1-methylpyrazolyl-5)methoxyimino acetic acid ethyl ester in 50 ml of methanol is added, dropwise, at 10°, with stirring, 1.76 g of triethylamine and then 1.89 g of 1,3-propane dithiol. After 2 hours, the crystallisate is separated on glass chips. The mother liquor is evaporated in vacuo. The remaining crystallisate is digested on the glass chips with a little ethanol and the filtrate is evaporated and the residue dried in vacuo to obtain the heading compound, m.p. 81°–83°.

(b) (3-Amino-1-methylpyrazolyl-5)methoxyimino acetic acid

To a solution of 3 g of (3-amino-1-methylpyrazolyl-5)methoxylimino acetic acid ethyl ester in 50 ml of methanol is added 940 mg of lithium hydroxide dissolved in 50 ml of water. After 2 hours reaction time, the solution is mixed with ion exchanger until the pH is 2.5. The ion exchanger is filtered off and the filtrate is evaporated in vacuo to obtain the heading compound.

(T) (5-Amino-1-methylpyrazolyl-3)methoxyimino acetic acid (for Example 27)

The heading compound is obtained in a manner analogous to that described under s) above.

(a) (5-Amino-1-methylpyrazolyl-3)methoxyimino acetic acid ethyl ester, m.p. 85°

(b) (5-Amino-1-methylpyrazolyl-3)methoxyimino acetic acid

EXAMPLE 44

In manner analogous to that described in Example 41, or 43, the compounds of Examples 36, 3, 40 and 23 may be obtained in substantially syn isomeric form.

What we claim is:
1. Compounds of formula I,

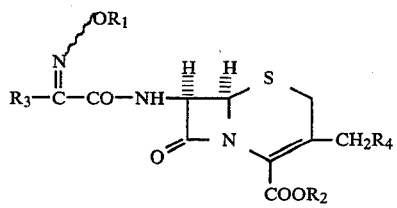

in which

R₁ is hydrogen, alkyl, phenylalkyl, carbalkoxyalkyl, $C_{2-5}$alkanoyl, alkoxy-carbonyl, carboxyalkyl, alkoxyalkyl, hydroxyalkyl, cyanoalkyl, or carbamoylalkyl, R₂ is hydrogen, pivaloyloxymethyl or the residue of an easily splittable ester grouping, R₃ is a 3- or 5-pyrazolyl radical, unsubstituted or mono- or di-substituted by alkyl, phenyl, alkoxy, alkylthio, carboxy, carboxyalkyl, carbamoyl, carbamoylalkyl, alkylsulphonyl, azido, $C_{2-5}$alkanoylamino, $C_{1-4}$alkoxycarbonylamino, benzylcarbonylamino, hydrazino, $C_{2-5}$alkanoylhydrazino, alkylidenhydrazino, phenyldenhydrazino, in which the phenyl nucleus is unsubstituted or substituted by NH₂, lower alkoxy or lower alkyl, furylidenhydrazino, carbalkoxy or a group $R_5R_6N$—, in which R₅ and R₆ are the same or different and are hydrogen or alkyl, provided that the nitrogen atoms and the 4-position of the pyrazole nucleus are either unsubstituted or substituted by alkyl, phenyl, or carbalkoxy, and R₄ is hydrogen, acetoxy, carbamoyloxy or —S—Rh, in which Rh is a heterocyclic radical, and pharmaceutically acceptable salts thereof.

2. A compound of claim 1, in syn isomeric form or in the form of a syn/anti isomeric mixture in which the syn isomer predominates.

3. The compound of claim 1, which is 7-{[(pyrazolyl-3)-syn-methoximino]acetylamino}-3-desacetoxy-3-(1-methyltetrazolyl-5-thio)cephalosporanic acid sodium salt.

4. The compound of claim 1, which is 7-{[(pyrazolyl-3)-syn-methoximino]acetylamino}-3-desacetoxy-3-(1-methyltetrazolyl-5-thio)cephalosporanic acid pivaloyloxy methyl ester.

5. The compound of claim 1, which is 7-{[(pyrazolyl-3)-syn-carbethoxymethoximino]acetylamino}-3-desacetoxy-3-(1-methyl-tetrazolyl-5-thio)cephalosporanic acid.

6. The compound of claim 1, which is 7-{[(pyrazolyl-3)-syn-carbethoxymethoximino]acetylamino}-3-desacetoxy-3-(1-methyltetrazolyl-5-thio)cephalosporanic acid pivaloyloxymethyl ester.

7. The compound of claim 1, which is 7-{](pyrazolyl-3-)-syn-carbamoylmethoximino]acetylamino}-3-desacetoxy-3-(1-methyl-tetrazolyl-5-thio)cephalosporanic acid.

8. A chemotherapeutic composition comprising an anti-bacterial effective amount of a compound of claim 1, in association with a chemotherapeutically acceptable diluent or carrier.

9. A method of inhibiting bacterial growth comprising administering to a subject in need of such treatment an anti-bacterially effective amount of a compound of claim 1.

10. The compound of claim 1 which is 7-[[(pyrazolyl-3)methoxyimino]acetylamino]-3-desacetoxy-3-(1-methyltetrazolyl-5-thio)cephalosporanic acid-trimethylacetoxymethyl ester.

11. A compound of claim 1 in which R₃ is a 3- or 5-pyrazolyl radical which is unsubstituted.

12. A compound of claim 1 in which R₄ is 1-methyltetrazolylthio.

13. A compound of claim 12 in which R₁ is alkyl, carbalkoxyalkyl or carbamoylalkyl.

14. A compound of claim 11, in which R₁ is alkyl, carbalkoxyalkyl or carbamoylalkyl and R₄ is 1-methyltetrazolylthio.

15. A compound of claim 14, in *syn* isomeric form or in the form of a *syn/anti* isomeric mixture in which the *syn* isomer predominates.

* * * * *